United States Patent
Bierer et al.

(10) Patent No.: US 6,844,468 B2
(45) Date of Patent: Jan. 18, 2005

(54) PROCESS FOR PREPARING SUBSTITUTED BENZOYL CHLORIDES

(75) Inventors: Lars Bierer, Liederbach (DE); Joachim Ritzer, Rodenbach (DE); Berthold Schiemenz, Frankfurt am Main (DE); Thomas Wessel, Niederdorfelden (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/264,086

(22) Filed: Oct. 3, 2002

(65) Prior Publication Data

US 2003/0130537 A1 Jul. 10, 2003

Related U.S. Application Data

(63) Continuation-in-part of application No. 09/915,830, filed on Jul. 26, 2001, now abandoned.

(30) Foreign Application Priority Data

Jul. 26, 2000 (DE) .......................................... 100 36 653

(51) Int. Cl.$^7$ .............................................. C07C 51/58
(52) U.S. Cl. ........................ 562/861; 562/862; 562/863
(58) Field of Search ................................ 562/861, 862, 562/863

(56) References Cited

U.S. PATENT DOCUMENTS

| 3,274,242 A | | 9/1966 | Etherington, Jr. et al. .. 260/544 |
| 5,599,981 A | * | 2/1997 | Fushimi et al. |
| 5,872,291 A | * | 2/1999 | Koshikawa et al. |

FOREIGN PATENT DOCUMENTS

GB 2 061 257 5/1981

* cited by examiner

Primary Examiner—Johann Richter
Assistant Examiner—Sikarl A. Witherspoon
(74) Attorney, Agent, or Firm—Richard P. Silverman

(57) ABSTRACT

The present invention relates to a process for preparing substituted benzoyl chlorides of the formula (1)

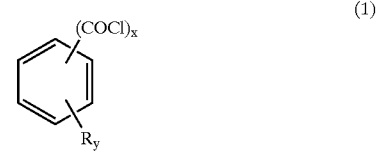

where R, x and y have the meaning given below, which comprises reacting a benzaldehyde of the formula (2)

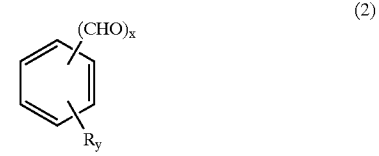

where R, independently of each other, is identical or different and is an unsubstituted phenyl radical or a phenyl radical that is substituted by halogen, $NO_2$, CN, ($C_1$–$C_4$)alkyl or ($C_1$–$C_4$)alkoxy, or is halogen, $NO_2$, CN, $NR'_2$, OR', $SO_2R'$, $SO_2OR'$, COR' or $CO_2R'$, where R' is an unbranched or branched $C_1$–$C_{10}$ alkyl radical, an unsubstituted phenyl radical or a phenyl radical which is substituted by halogen, $NO_2$, CN, ($C_1$–$C_4$)alkyl or ($C_1$–$C_4$)alkoxy, x is 1 or 2 and y is 1, 2 or 3, with a chlorinating agent in the presence of a free-radical initiator and a solvent at from −20 to +200° C.

16 Claims, No Drawings

PROCESS FOR PREPARING SUBSTITUTED BENZOYL CHLORIDES

CROSS REFERENCE TO RELATED APPLICATION

This application is a continuation in part of U.S. Ser. No. 09/915,830, filed Jul. 26, 2001 now abandoned, the entire disclosure of which is incorporated herein by reference.

BACKGROUND OF THE INVENTION

The present invention relates to a process for preparing substituted benzoyl chlorides by chlorinating the corresponding benzaldehydes. Substituted benzoyl chlorides may be considered activated derivatives of the corresponding benzoic acids. For this reason they are widely used as valuable synthesis building blocks, for example as intermediates for producing plant protection agents and drugs and for producing dyes and plastics.

Aromatic carboxylic acid chlorides are customarily prepared by reacting carboxylic acids with a chlorinating agent or by partial hydrolysis of benzotrichlorides. An important advantage of these processes is based on the fact that the corresponding starting materials are available on an industrial scale, because they are easily accessible. These favorable preconditions are not present in the case of preparation of substituted benzoyl chlorides, since the corresponding starting materials, i.e. appropriately substituted carboxylic acids or benzotrichlorides are generally not readily accessible and also are not usually available in industrial quantities.

It is known that starting from aldehydes, by halogenating the aldehyde group, carboxylic acid halides are accessible directly.

SUMMARY OF THE INVENTION

Thus EP 0 723 950 B1 describes a process for preparing alkylbenzoyl chlorides by chlorinating alkylbenzaldehydes. Although in this case the reaction is carried out in the presence of a solvent and a further methyl- or chloromethyl-substituted benzene derivative, the selectivity never exceeds 86%. Owing to the use of a complex mixture of substances (at least 4 components) and the not very high selectivities, purification of the reaction product is very costly and the product quality is adversely affected.

The reaction of alkylbenzaldehydes with chlorine in the presence of a solvent and an inert gas leads only to moderate selectivities of benzoyl chlorides (see example 3 in EP 0 849 253 A1:81%). As a result, its ability to be carried out industrially becomes uneconomic.

A process for preparing 3-chloro-4-fluorobenzoyl chloride is described in EP 0 922 693 A1. In this case the precursor 4-fluorobenzoyl chloride is prepared by chlorinating 4-fluorobenzaldehyde. However, 8.3% of a minor component are also formed, (they are identified as 4,4'-difluorobenzil) which makes purifying the product more difficult. When 4-fluorobenzaldehyde is chlorinated in the absence of a solvent, a gel-like solid forms with intensive foam formation (see comparative example 3 in the experimental part). A further disadvantage is the significantly increased formation of a chlorine byproduct (no 4,4'-difluorobenzil) and the associated markedly worsened selectivity.

The use of ortho-halo-substituted benzaldehydes, i.e. 2-halo-benzaldehydes (in which a halogen is in the ortho position to the aldehyde group) gives an additional problem. This is because these aldehydes have a tendency in part to dehalogenate (see comparative example 1a in the experimental part), which forms products which are frequently very difficult to separate off and thus adversely affect the quality of the end products, which is subject to very high requirements for use in the syntheses for pharmaceutical products or plant protection agents.

Furthermore, in the chlorination, one or more byproducts (termed minor components in the experimental part) are frequently formed, which are assumed to be secondary products of uncontrolled reactions between the benzoyl chloride prepared and still unreacted starting product (substituted benzaldehyde), possibly with the participation of chlorine. In particular, a chlorinated byproduct is formed. As shown in comparative examples 1a, 1b, 2a and 2b, this adversely affects the selectivity of the reaction.

In view of the above described disadvantages and problems, there is a need to provide a process which avoids these disadvantages and problems and which, without requiring great additional expense, may be implemented in a simple manner and which makes the desired products accessible in high yields with high conversion rate and high selectivity.

DESCRIPTION OF THE PREFERRED EMBODIMENTS

This object is surprisingly achieved by a process for preparing substituted benzoyl chlorides of the formula (1)

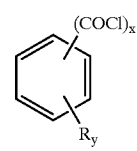

(1)

where R, x and y have the meaning given below, which comprises reacting a benzaldehyde of the formula (2)

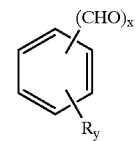

(2)

where R, independently of each other, is identical or different and is an unsubstituted phenyl radical or a phenyl radical that is substituted by halogen, $NO_2$, CN, ($C_1$–$C_4$)alkyl or ($C_1$–$C_4$)alkoxy, or is halogen, $NO_2$, CN, $NR'_2$, OR', $SO_2R'$, $SO_2OR'$, COR' or $CO_2R'$, where R' is an unbranched or branched $C_1$–$C_{10}$ alkyl radical, an unsubstituted phenyl radical or a phenyl radical which is substituted by halogen, $NO_2$, CN, ($C_1$–$C_4$)alkyl or ($C_1$–$C_4$)alkoxy, x is 1 or 2 and y is 1, 2 or 3, with a chlorinating agent in the presence of a free-radical initiator and a solvent at from −20 to +200° C.

R, x and y thus have the same meaning in formula (1) as in formula (2).

The inventive process has a plurality of advantages. Firstly, it may be applied to a relatively large number of substituted benzaldehydes, and secondly it is surprisingly possible to carry out the reaction with great success even at comparatively low temperatures (see examples 1 to 4). The low temperatures make a particularly gentle reaction possible, which is of particular advantage for sensitive benzaldehydes, for example for halogenated benzaldehydes having a tendency to dehalogenate. Although it is possible by employing low temperatures to effectively decrease the dehalogenation, even in the absence of a solvent (see comparative examples 1b, 2a and 2b), the formation of unwanted byproducts, identified as minor components, cannot be decreased to the desired extent. As shown by a comparison between comparative example 1b and example 1, and between comparative example 2b and example 2, the inventive procedure (in the presence of a solvent) leads to a surprisingly high reduction of the unwanted byproducts, which form in only negligible amounts. A similar result can also be seen in comparative example 3 and example 3, where the formation of the minor components can be reduced to roughly one-tenth of the value formed in comparative example 3. Here also there is a drastic reduction in unwanted byproducts, identified as minor components.

As examples 5, 6 and 7 prove, benzaldehydes which are halogenated ortho to the aldehyde group may be reacted even at relatively high temperatures, at which no dehalogenation occurs and in addition unwanted byproducts are formed only to a slight or very slight extent.

In the inventive process, very successfully, a benzaldehyde of the formula (2) may be used, where R, independently of each other, is identical or different and is halogen, $NO_2$, CN, $NR'_2$, OR', $SO_2R'$, $SO_2OR'$, COR' or $CO_2R'$, where R' is an unbranched or branched $C_{1-4}$ alkyl radical or an unsubstituted phenyl radical.

In particular, a benzaldehyde of the formula (2), can be used, where R independently of one another is identical or different and is halogen, $NO_2$, CN, OR' or COR', where R' is an unbranched or branched $C_1-C_4$ alkyl radical or an unsubstituted phenyl radical.

Particular interest is attached to benzaldehydes (2) where x is 1.

Interest is in addition attached to benzaldehydes (2) where y is 1 or 2, or 2 or 3, in particular where y is 1 or 2, preferably 2.

Also, a benzaldehyde (2) can be used very successfully where at least one of the radicals R is a halogen, in particular F, Cl or Br, preferably F or Cl, in an ortho position to an aldehyde group, in particular where one of the radicals R is a halogen in an ortho position to an aldehyde group and a second of the radicals R is also halogen and halogen is F, Cl or Br, in particular F or Cl.

A highly suitable benzaldehyde (2) is where R, independently of each other, is identical or different and is F, $C_1$ or $NO_2$, x is 1 and at least one of the radicals R is an F or Cl in an ortho position to an aldehyde group.

Customarily, the substituted benzaldehyde (2) and the chlorinating agent are used in a molar ratio of 1:(0.5 to 2.0), in particular 1:(0.7 to 1.5), preferably 1:(0.9 to 1.2).

The chlorinating agent can be chlorine, or a chlorine-releasing agent, in the presence or absence of an inert dilution gas such as nitrogen, carbon dioxide, or a noble gas. Preferably, the procedure is carried out in the absence of an inert dilution gas. Surprisingly when the reaction is carried out in the absence of an inert dilution gas the selectivity and conversion rate is very high see examples 8 through 12. Suitable chlorinating agents, without making any claim to completeness, are $Cl_2$, $SOCl_2$, $SO_2Cl_2$, $PCl_3$, $POCl_3$, $PCl_5$, $SbCl_5$, ICl, $ICl_3$, $SCl_2$, $S_2Cl_2$, $MnCl_4$, $(C_1-C_4)$ alkylhypochlorite, $CCl_4$ and N-chlorosuccinimide or a mixture of same.

The procedure can be carried out in the presence of an inert dilution gas. When the reaction is carried out in an inert dilution gas the selectivity and conversion rate remain good see examples 1 through 7.

In particular, $Cl_2$, $SOCl_2$, $SO_2CO_2$ or a mixture of same are used as chlorinating agents.

It has proved to be particularly expedient to react the substituted benzaldehyde (2) with $Cl_2$ as chlorinating agent.

Substituted benzaldehydes are reacted with the chlorinating agent in a manner of a free-radical chlorination, the presence of a free-radical initiator being advantageous. Usually, a peroxide or an azo compound is used individually, or in combination with one another, as free-radical initiator. It is known that organic peroxides and organic azo compounds decompose under the effects of heat and/or light into free radicals, which initiate the free-radical chlorination.

Examples of suitable peroxides and organic azo compounds are, without making any claim to completeness, ethyl methyl ketone peroxide, tert-butyl hydroperoxide, tert-butyl trimethylsilyl peroxide, cumene hydroperoxide, lauroyl peroxide, dibenzoyl peroxide, ditert-butyl peroxide, dilauryl peroxide, perbenzoic acid tert-butyl ester, tert-butyl peroxy-2-ethylhexanoate, 2,2'-azobis(4-methoxy-2,4-dimethylvaleronitrile), 2,2'-azobis(2,4-dimethylvaleronitrile), 2,2'-azobis(isobutyronitrile), dimethyl-2,2'-azobis(isobutyrate), 2,2'-azobis(2-methylbutyronitrile), 1,1'-azobis(1-cyclohexanecarbonitrile), 2-(carbamoylazo)isobutyronitrile, 2,2'-azobis(2,4,4-trimethylpentane), 2,2'-azobis (isobutyroamidine) dihydrochloride, 2,2'-azobis(N,N'-dimethylenisobutyroamidine) dihydrochloride, 2,2'-azobis (2-amidinopropane) dihydrochloride, 2,2'-azobis(N,N'-dimethylenisobutyroamidine), 4,4'-azobis(4-cyanopentanoic acid) and/or 2,2'-azobis[2-methyl-N-(2-hydroxyethyl)propionamide], in particular tert-butyl hydroperoxide, dibenzoyl peroxide, dilauryl peroxide, tert-butyl peroxy-2-ethylhexanoate, 2,2'-azobis(4-methoxy-2,4-dimethylvaleronitrile), 2,2'-azobis(2,4-dimethylvaleronitrile) and/or 2,2'-azobis(isobutyronitrile).

According to a preferred variant, 2,2'-azobis(2,4-dimethylvaleronitrile), 2,2'-azobis(isobutyronitrile) and/or 2,2'-azobis(4-methoxy-2,4-dimethylvaleronitrile) are used as free-radical initiators.

The free-radical initiator (peroxide and/or azo compound) is usually used in an amount of from 0.001 to 10, in particular from 0.005 to 5, preferably from 0.02 to 2 mol percent, based on the substituted benzaldehyde (2).

The substituted benzaldehydes (2) are reacted with the chlorinating agent in the presence of a solvent which is inert under reaction conditions. The solvent used is a monochlorinated or polychlorinated aliphatic or aromatic hydrocarbon or a mixture of same. Examples of suitable solvents are, without making a claim to completeness, 1,2-dichloroethane, methyl chloride, methylene chloride, chloroform, carbon tetrachloride, chlorobenzene, dichlorobenzenes, trichlorobenzenes and chlorotoluenes.

The solvent used is in particular chlorobenzene, 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, 2-chlorotoluene, 3-chlorotoluene, 4-chlorotoluene or a mixture of the same, preferably chlorobenzene, 1,2-dichlorobenzene, 1,3-dichlorobenzene, 1,4-dichlorobenzene or a mixture of the same.

According to a particularly preferred variant, chlorobenzene is used as solvent. The solvent is usually used in a ratio of from 50:1 to 1:50, in particular from 10:1 to 1:10, preferably from 4:1 to 1:4, based on the substituted benzaldehyde.

In a multiplicity of cases it has proved to be sufficient to react the substituted benzaldehydes (2) with the chlorinating agent at from −10 to 130° C., in particular at from 0 to 120° C., preferably from 20 to 90° C., particularly preferably from 30 to 85° C.

A multiplicity of substituted benzaldehydes may be reacted very successfully at a temperature of from 35 to 80° C.

The resultant substituted benzoyl chlorides (1) can be isolated by conventional workup processes which depend on the melting and boiling points of the products or, when employing solvents, on the solubility of the product in the solvent used and, in turn, on its melting point/boiling point. Usual workup processes in this case are chromatography, filtration, phase separation, centrifugation or distillation at atmospheric pressure or under reduced pressure. In particular, work up by distillation is the method of choice for substituted benzoyl chlorides.

The inventive process may be carried out batchwise or continuously. All process steps can be carried out at atmospheric pressure, reduced pressure or superatmospheric pressure.

The examples below describe the process without restricting it:

EXAMPLES

Experimental Part

Comparative Example 1a 552.3 g of 2,6-difluorobenzaldehyde are introduced under protective gas into a column chlorination apparatus (height 60 cm, diameter 5 cm) and 2.3 g of 2,2'-azobis(2,4-dimethylvaleronitrile) are added with stirring. The mixture is then heated to 67° C. internal temperature and, in the course of 7 hours, a total of 290 g of chlorine are introduced. The chlorine is added at a rate of 14 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 2.4% | (a/a) | 2,6-difluorobenzaldehyde |
|---|---|---|---|
| | 85.1% | (a/a) | 2,6-difluorobenzoyl chloride |
| | 1.1% | (a/a) | 2-fluorobenzoyl chloride |
| | 10.7% | (a/a) | minor component |
| Conversion rate: | 97.6% | | |
| Selectivity: | 87.2% | | |

Comparative Example 1b 552.7 g of 2,6-difluorobenzaldehyde are introduced under protecting gas into a column chlorination apparatus (height 60 cm, diameter 5 cm) and 2.3 g of 2,2'-azobis(2,4-dimethylvaleronitrile) are added with stirring. The mixture is then heated to 51° C. internal temperature and, in the course of 7 hours, a total of 292 g of chlorine are introduced. The chlorine is added at a rate of 14 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 1.8% | (a/a) | 2,6-difluorobenzaldehyde |
|---|---|---|---|
| | 92.1% | (a/a) | 2,6-difluorobenzoyl chloride |
| | 5.7% | (a/a) | minor component |
| Conversion rate: | 98.2% | | |
| Selectivity: | 93.8% | | |

Example 1

555.2 g of 2,6-difluorobenzaldehyde in 370 g of chlorobenzene are introduced under protecting gas into a column chlorination apparatus (height 60 cm, diameter 5 cm) and 2.4 g of 2,2'-azobis(2,4-dimethylvaleronitrile) are added with stirring. The mixture is then heated to 51° C. internal temperature and, in the course of 7 hours, a total of 295 g of chlorine are introduced. The chlorine is added at a rate of 14 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 0.2% | (a/a) | 2,6-difluorobenzaldehyde |
|---|---|---|---|
| | 98.9% | (a/a) | 2,6-difluorobenzoyl chloride |
| | 0.8% | (a/a) | minor component |
| Conversion rate: | 99.8% | | |
| Selectivity: | 99.1% | | |
| Yield: | 96.7% | | |

There then follows the product distillation under reduced pressure via a packed column (height 100 cm, packing Sulzer CY) at a reflux ratio of 1:7, 2,6-difluorobenzoyl chloride boiling at a constant 125° C. at 145 mbar. The fractionated 2,6-difluorobenzoyl chloride has a purity of >99.5% (a/a).

Comparative Example 2a 249.8 g of 2-fluorobenzaldehyde are introduced under protecting gas into a 500 ml flask and 0.9 g of 2,2'-azobis(isobutyronitrile) are added with stirring. The mixture is then heated to 59° C. internal temperature and in the course of 8 hours a total of 152 g of chlorine are introduced. The chlorine is added at a rate of 7 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 1.5% | (a/a) | 2-fluorobenzaldehyde |
|---|---|---|---|
| | 65.6% | (a/a) | 2-fluorobenzoyl chloride |
| | 31.0% | (a/a) | minor component |
| Conversion rate: | 98.5% | | |
| Selectivity: | 66.6% | | |

Comparative Example 2b 247.3 g of 2-fluorobenzaldehyde are introduced under protecting gas into a 500 ml flask and 1.0 g of 2,2'-azobis (2,4-dimethylvaleronitrile) are added with stirring. The mixture is then heated to 40° C. internal temperature and in the course of 8 hours a total of 150 g of chlorine are introduced. The chlorine is added at a rate of 7 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 1.7% | (a/a) | 2-fluorobenzaldehyde |
|---|---|---|---|
| | 85.6% | (a/a) | 2-fluorobenzoyl chloride |
| | 12.6% | (a/a) | minor component |
| Conversion rate: | 98.3% | | |
| Selectivity: | 87.1% | | |

Example 2

248.0 g of 2-fluorobenzaldehyde in 900 g of chlorobenzene are introduced under protecting gas into a 2 l flask and 1.0 g of 2,2'-azobis(2,4-dimethylvaleronitrile) is added with stirring. The mixture is then heated to 40° C. internal temperature, and in the course of 8 hours a total of 150 g of chlorine are introduced. The chlorine is added at a rate of 7 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 1.0% | (a/a) | 2-fluorobenzaldehyde |
|---|---|---|---|
| | 98.4% | (a/a) | 2-fluorobenzoyl chloride |
| | 0.6% | (a/a) | minor component |
| Conversion rate: | 99.0% | | |
| Selectivity: | 99.4% | | |

Comparative Example 3

829.1 g of 4-fluorobenzaldehyde are introduced under protecting gas into a column chlorination apparatus (height 60 cm, diameter 5 cm; filling level 55 cm) and 2.7 g (0.16 mol percent) of 2,2'-azobis(2,4-dimethylvaleronitrile) are added with stirring. The mixture is then heated to 42° C. internal temperature and chlorine is introduced. The chlorine is added at a rate of 12 liters/hour. Already after 2.5 hours, a gel-like solid forms with vigorous foaming, which leads to the introduction of chlorine needing to be terminated after 13 hours.

The progress of the reaction is monitored by gas-chromatographic analysis (GC).

| GC conversion rate monitoring: | 10.7% | (a/a) | 4-fluorobenzaldehyde |
|---|---|---|---|
| | 66.2% | (a/a) | 4-fluorobenzoyl chloride |
| | 22.2% | (a/a) | minor component |
| Conversion rate: | 89.3% | | |
| Selectivity: | 74.1% | | |

Example 3

402.2 g of 4-fluorobenzaldehyde in 400 g of chlorobenzene are introduced under protecting gas into a column chlorination apparatus (height 60 cm, diameter 5 cm; filling level 55 cm) and 1.3 g (0.16 mol percent) of 2,2'-azobis(2,4-dimethylvaleronitrile) are added with stirring. The mixture is then heated to 42° C. internal temperature and in the course of 7 hours a total of 240 g of chlorine are introduced. The chlorine is added at a rate of 11 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 0.5% | (a/a) | 4-fluorobenzaldehyde |
|---|---|---|---|
| | 97.1% | (a/a) | 4-fluorobenzoyl chloride |
| | 2.4% | (a/a) | minor component |
| Conversion rate: | 99.5% | | |
| Selectivity: | 97.6% | | |
| Yield: | 95.3% | | |

The product is then distilled under reduced pressure via a packed column (height 100 cm, packing Sulzer CY) at a reflux ratio of 1:15, with 4-fluorobenzoyl chloride boiling at a constant 94° C. at 40 mbar. The fractionated 4-fluorobenzoyl chloride has a purity of >99.5% (a/a).

Example 4

310 g of 2-chlorobenzaldehyde in 300 g of chlorobenzene are introduced under protecting gas into a 1 l flask and 1.1 g of 2,2'-azobis(2,4-dimethylvaleronitrile) are added with stirring. The mixture is then heated to 41° C. internal temperature and, in the course of 7 hours, a total of 164 g of chlorine are introduced. The chlorine is added at a rate of 8 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 5.0% | (a/a) | 2-chlorobenzaldehyde |
|---|---|---|---|
| | 93.0% | (a/a) | 2-chlorobenzoyl chloride |
| | 1.1% | (a/a) | minor component |
| Conversion rate: | 95.0% | | |
| Selectivity: | 97.9% | | |

Example 5

200.4 g of 2,6-dichlorobenzaldehyde in 650 g of chlorobenzene are introduced under protecting gas into a column chlorination apparatus (height 60 cm, diameter 5 cm) and 1.2 g of 2,2'-azobis(isobutyronitrile) are added with stirring. The mixture is then heated to 80° C. internal temperature and, in the course of 6 hours, a total of 85 g of chlorine are introduced. The chlorine is added at the rate of 5 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 0.1% | (a/a) | 2,6-dichlorobenzaldehyde |
|---|---|---|---|
| | 99.0% | (a/a) | 2,6-dichlorobenzoyl chloride |
| | 0.9% | (a/a) | minor component |
| Conversion rate: | 99.9% | | |
| Selectivity: | 99.1% | | |

Example 6

200.6 g of 2-chloro-6-fluorobenzaldehyde in 600 g of chlorobenzene are introduced under protecting gas in to a column chlorination apparatus (height 60 cm, diameter 5 cm) and 1.0 g of 2,2'-azobis(isobutyronitrile) is added with stirring. The mixture is then heated to 70° C. internal temperature and, in the course of 7 hours, a total of 95 g of chlorine are introduced. The chlorine is added at a rate of 5 liters/hour. Unreacted chlorine is then blown out with protecting gas and the reaction mixture is cooled to room temperature.

The progress of the reaction is monitored by gas-chromatographic analysis (GC).

| GC conversion rate monitoring: | 0.2% | (a/a) | 2-chloro-6-fluorobenzaldehyde |
|---|---|---|---|
| | 98.4% | (a/a) | 2-chloro-6-fluorobenzoyl chloride |
| | 1.2% | (a/a) | minor component |
| Conversion rate: | 99.8% | | |
| Selectivity: | 98.6% | | |

Example 7

50.1 g of 2-chloro-5-nitrobenzaldehyde in 200 g of chlorobenzene are introduced under protecting gas into a 500 ml flask and 0.6 g of 2,2'-azobis(isobutyronitrile) is added with stirring. The mixture is then heated to 80° C. internal temperature and, in the course of 3 hours, a total of 20 g of chlorine are introduced. The chlorine is added at a rate of 3 liters/hour. Unreacted chlorine is then blown out with protecting gas and the reaction mixture is cooled to room temperature. The progress of the reaction is monitored by gas-chromatographic analysis (GC).

| GC conversion rate monitoring: | 55.1% | (a/a) | 2-chloro-6-nitrobenzaldehyde |
|---|---|---|---|
| | 42.3% | (a/a) | 2-chloro-6-nitrobenzoyl chloride |
| | 1.6% | (a/a) | minor component |
| Conversion rate: | 44.9% | | |
| Selectivity: | 94.2% | | |

Examples Without Inert Gas

Inert gas was used solely after the reaction for blowing out unreacted chlorine.

Example 8

In a column chlorination apparatus (height 60 cm, diameter 5 cm) 555 g 2,6-difluoro-benzaldehyde are introduced in 370 g chlorobenzene and 2.4 g 2,2'azobis(2,4 dimethylvaleronitrile) are added with stirring. The mixture is then heated to 50° C. (interior temperature), and, in the course of 7 hours, a total of 295 g chlorine are introduced. The Chlorine is added at a rate of 14 litres/hour. Unreacted chlorine is then blown out with dry nitrogen and the reaction is cooled to room temperature. The progress is monitored by gas-chromatographic analysis (GC).

| GC conversion rate monitoring: | 0.6% | (a/a) | 2,6-difluorobenzaldehyde |
|---|---|---|---|
| | 98.1% | (a/a) | 2,6-difluorobenzoyl chloride |
| | 0.8% | (a/a) | minor component |
| Conversion rate: | 99.4% | | |
| Selectivity: | 98.7% | | |

The product is then distilled under a vacuum via a packed column (height 100 cm, packing Sulzer CY) at a reflux ratio of 1:7, 2,6-difluoro-benzoyl chloride boiling at a constant 125° C. at 145 mbar. The fractionated 2,6-difluor-benzoyl chloride has a purity of >99.5% (a/a). The yield is 96.7%.

Example 9

248.1 g of 2-fluorobenzaldehyde and 1.0 g of 2,2'-azobis (2,4 dimethylvaleronitrile) are introduced into a 2l flask with 900 g chlorobenzene.

The mixture is then heated to 40° C. (interior temperature), and, in the course of 8 hours, a total of 150 g chlorine are introduced. The chlorine is added at a rate of 7 litres/hour. The progress is monitored by GC.

| GC conversion rate monitoring: | 0.8% | (a/a) | 2-Fluorobenzaldehyde |
|---|---|---|---|
| | 97.9% | (a/a) | 2-Fluorobenzoylchloride |
| | 0.9% | (a/a) | minor component |
| Conversion rate: | 99.2% | | |
| Selectivity: | 98.7% | | |

Example 10

In a column chlorination apparatus (height 60 cm, diameter 5 cm) 401.9 g 4-fluoro-benzaldehyde are introduced in 400 g chlorobenzene and 1.2 g 2,2'-azobis(2,4 dimethylvaleronitrile) are added with stirring. The mixture is then heated to 41° C. (interior temperature), and, in the course of 7 hours, a total of 250 g chlorine are introduced. The chlorine is added at a rate of 12 litres/hour. The progress is monitored by gas-chromatographic analysis (GC).

| GC conversion rate monitoring: | 0.6% | (a/a) | 4-fluorobenzaldehyde |
|---|---|---|---|
| | 96.5% | (a/a) | 4-fluorobenzoyl chloride |
| | 2.4% | (a/a) | minor component |
| Conversion rate: | 95.7% | | |
| Selectivity: | 97.3% | | |
| Yield: | 93.5% | | |

Example 11

312 g of 2-chlorobenzaldehyde and 300 g of chlorobenzene are introduced into a 1l flask and 1.1 g of 2,2'-azobis (2,4 dimethylvaleronitril) are added with stirring. The mixture is then heated to 43° C. (interior temperature), and, in the course of 7 hours, a total of 169 g chlorine are introduced. The Chlorine is added at a rate of 9 litres/hour. The progress is monitored by GC. After conversion the unreacted cloride is removed from the product via a vacuum and separated by vacuum-distillation.

| GC conversion rate monitoring: | 4.3% | (a/a) | 2-chlorobenzaldehyde |
|---|---|---|---|
| | 93.1% | (a/a) | 2-chlorobenzoyl chloride |
| | 1.3% | (a/a) | minor component |
| Conversion rate: | 95.7% | | |
| Selectivity: | 97.3% | | |
| Yield: | 93.5% | | |

Example 12

In a column chlorination apparatus (height 60 cm, diameter 5 cm) 200 g 2,6-dicloro-benzaldehyde are introduced in 650 g chlorobenzene and 1.2 g 2,2' azobis(isobutyronitrile) are added with stirring. The mixture is then heated to 80° C. (interior temperature), and, in the course of 6 hours, a total of 89 g chlorine are introduced. The Chlorine is added at a rate of 6 litres/hour. Unreacted chlorine is then blown out with dry nitrogen and the reaction is cooled to room temperature. The progress is monitored by gas-chromatographic analysis (GC).

| GC conversion rate monitoring: | 0.1% | (a/a) | 2,6-difluorobenzaldehyde |
|---|---|---|---|
| | 98.5% | (a/a) | 2,6-difluorobenzoyl chloride |
| | 0.8% | (a/a) | minor component |
| Conversion rate: | 99.9% | | |
| Selectivity: | 98.6% | | |

What is claimed is:

1. A process for preparing substituted berizoyl chlorides of the formula (1)

(1)

where R, x and y have the meaning given below, which comprises heating in the presence of a chlorinating agent and reacting a benzaldehyde of the formula (2)

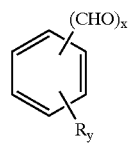

(2)

where R, independently of each other, is identical or different and is a phenyl radical that is substituted by halogen, $NO_2$, CN, or as halogen, $NO_2$, CN, $NR'_2$, OR', $SO_2R'$, $SO_2OR'$, COR' or $CO_2R'$, where R' is an unbranched or branched $C_1$–$C_{10}$ alkyl radical, an unsubstituted phenyl radical or a phenyl radical which is substituted by halogen, $NO_2$, CN, ($C_1$–$C_4$)alkyl or ($C_1$–$C_4$)alkoxy, x is 1 or 2 and y is 1, 2 or 3, where if R is halogen, then all halogens are identical or if R is different, then only one R may be a halogen or all the R halogens are identical, and one or more R is selected from the group of: $NO_2$, CN, ($C_1$–$C_4$)alkyl or ($C_1$–$C_4$)alkoxy;
with said chlorinating agent in the presence of a free-radical initiator and a solvent, in the absence of an inert dilution gas, at a reaction temperature from −20 to ×200° C.

2. The process as claimed in claim 1, wherein the benzaldehyde of the formula (2) is used, where R independently of each other is identical or different and is halogen, $NO_2$, CN, $NR'_2$, OR', $SO_2R'$, $SO_2OR'$, COR' or $CO_2R'$, where R' is an unbranchod or branched $C_1$–$C_4$ alkyl radical or an unsubstituted phenyl radical, if R is halogen, then all halogens are identical or if R is different, then only one R may be a halogen or all the R halogens are identical and one or R is selected from the group of: $NO_2$, CN, ($C_1$–$C_4$)alkyl or ($C_1$–$C_4$)alkoxy.

3. The process as claimed in claim 1, wherein a benzaldehyde (2) is used where x is 1.

4. The process as claimed in claim 1, wherein a benzaldehyde (2) is used where at least one of the radicals R is a halogen in an ortho position to an aldehyde group.

5. The process as claimed in claim 1, wherein a benzaldehyde (2) is used where R independently of each other is identical and is F, Cl or $NO_2$, or R independently of each other is different and is F or Cl with $NO_2$ x is 1 and at least one of the radicals R is an F or Cl in ortho position to the aldehyde group, where if R is halogen, then all halogens are identical or if R is different, then only one R may be a halogen or all the R halogens are identical and one or more R is selected from the group consisting of: $NO_2$, CN, ($C_1$–$C_4$)alkyl, ($C_1$–$C_4$)alkoxy, and mixtures thereof.

6. The process as claimed in claim 1, wherein the chlorinating agent is selected from the group consisting of $Cl_2$, $SOCl_2$, $SO_2Cl_2$, $PCl_3$, $POCl_3$, $PCl_5$, $SbCl_5$, ICl, $ICl_3$, $SCl_2$, $S_2Cl_2$, $MnCl_4$, ($C_1$–$C_4$)alkyl hypochlorite, $CCl_4$, N-chlorosuccinimide, and mixtures thereof.

7. The process as claimed in claim 1, wherein the chlorinating agent is selected from the group consisting of $Cl_2$, $SOCl_2$, $SO_2Cl_2$, and mixtures thereof.

8. The process as claimed in claim 1, wherein the free-radical initiator used is an organic peroxide or an organic azo compound or a mixture of the same.

9. The process as claimed in claim 1, wherein the free-radical initiator is selected from the group consisting of 2,2'-azobis(2,4-dimethylvaleronitrile), 2,2'-azobis (isobutyronitrile), 2,2-azobis(4-methoxy-2,4-dimethylvaleronitrile), and mixtures thereof.

10. The process as claimed in claim 1, wherein the solvent is selected from the group consisting of a monochlorinated or polychlorinated aliphatic or aromatic hydrocarbon, and mixtures thereof.

11. The process as claimed in claim 1, wherein the solvent is selected from the group consisting of chlorobenzene, 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, 2-chlorotoluene, 3-chlorotoluene, 4-chlorotoluene, and mixtures thereof.

12. The process as claimed in claim 1, wherein the reaction temperature is 0 to 120° C.

13. The process as claimed in claim 1, wherein the reaction temperature is from 20 to 90° C.

14. A process for preparing substituted benzoyl chlorides of the formula (1)

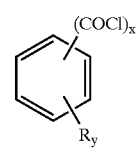

(1)

where R, x and y have the meaning given below, which comprises heating in the presence of a chlorinating agent and reacting a benzaldehyde of the formula (2)

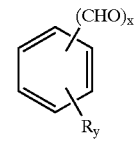

(2)

where R, independently of each other, is identical or different and is a phenyl radical that is substituted by halogen, $NO_2$, CN, or is halogen, $NO_2$, CN, $NR'_2$, OR', $SO_2R'$, $SO_2OR'$, COR' or $CO_2R'$, where R' is an unbranched or branched $C_1$–$C_{10}$ alkyl radical, an unsubstituted phenyl radical or a phenyl radical which is substituted by halogen, $NO_2$, CN, ($C_1$–$C_4$) alkyl or ($C_1$–$C_4$)alkoxy, x is 1 or 2 and y is 1, 2 or 3, with chlorinating agent in the presence of an inert dilution gas, in the presence of a free-radical initiator, and a solvent at a reaction temperature from −20 to ×200° C.

15. The process as claimed in claim 14, wherein the benzaldehyde of the formula (2) is used, where R independently of each other is identical or different and is halogen, $NO_2$, CN, $NR'_2$, OR', $SO_2R'$, $SO_2OR'$, COR' or $CO_2R'$, where R' is an unbranched or branched $C_1$–$C_4$ alkyl radical or an unsubstituted phenyl radical, if R is halogen, then all halogens are identical or if R is different, then only one R may be a halogen and one or more other compounds selected from the group consisting of $NO_2$, CN, $(C_1$–$C_4)$alkyl, $(C_1$–$C_4)$alkoxy, and mixtures thereof.

16. The process as claimed in claim 14, wherein a benzaldehyde (2) is used where x is 1 and where at least one of the radicals R is a halogen in an ortho position to an aldehyde group.

* * * * *